United States Patent [19]

Stoller et al.

[11] Patent Number: 4,936,774

[45] Date of Patent: Jun. 26, 1990

[54] ORTHODONTIC MIRROR IMAGE BRACKETS TO REMOVABLY RECEIVE THE END PORTIONS OF LINGUAL ARCH WIRES

[76] Inventors: Arnold E. Stoller, 2150 Shore Ave., Freeland, Wash. 09249; John L. Stoller, 901 Sunset Dr., Blue Bell, Pa. 19422

[21] Appl. No.: 299,485

[22] Filed: Jan. 23, 1989

Related U.S. Application Data

[63] Continuation-in-part of Ser. No. 30,442, Mar. 25, 1987, Pat. No. 4,799,883.

[51] Int. Cl.[5] ................................................. A61C 7/00
[52] U.S. Cl. ........................................... 433/11; 433/17
[58] Field of Search ....................................... 433/11, 17

[56] References Cited

U.S. PATENT DOCUMENTS 3,052,028  9/1962  Wallshein ............................. 433/11
3,464,113  9/1969  Silverman et al. .................... 433/11

Primary Examiner—Robert Peshock
Attorney, Agent, or Firm—Shlesinger & Myers

[57] ABSTRACT

An orthodontic bracket comprises a body having first and second ends, a first vertical sidewall for attachment to a molar band, and a second sidewall extending arcuate and upwardly away from a lower portion of the first sidewall. A contoured slot extends between the ends and downwardly from an upper portion of the first sidewall for defining an upper and a lower channel, and the lower channel permits the second sidewall to flex outwardly relative to the first sidewall. The upper channel includes a lower arcuate surface upon which an orthodontic wire seats. The second sidewall includes a pawl overlying the upper channel and extending substantially the length thereof for engaging and maintaining an orthodontic wire in the upper channel and against the lower arcuate surface.

17 Claims, 3 Drawing Sheets

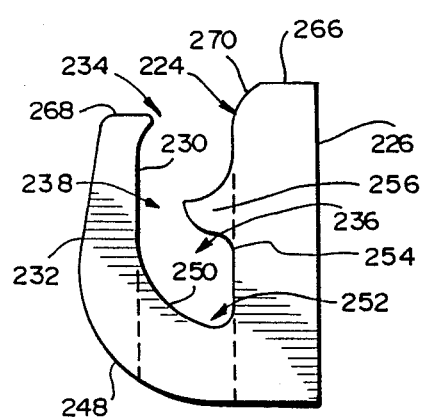
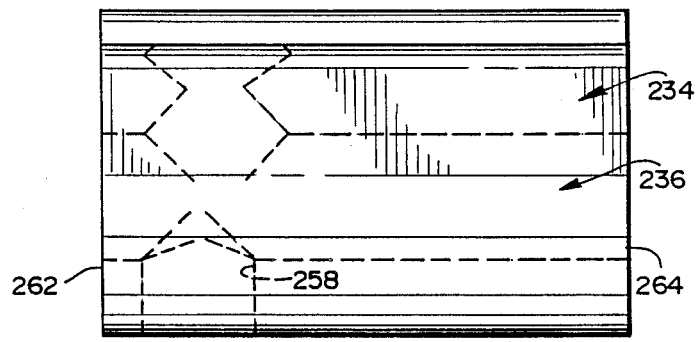
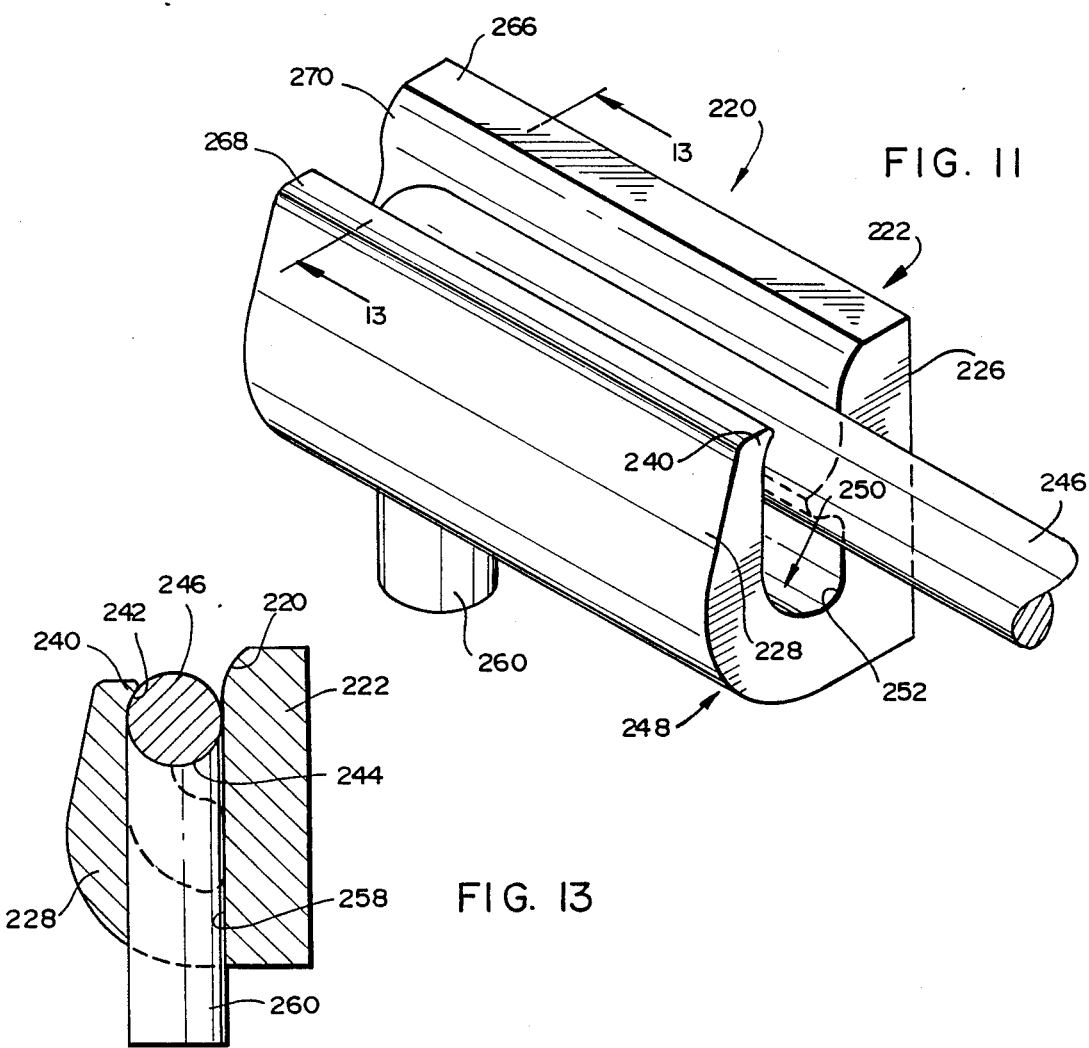

ORTHODONTIC MIRROR IMAGE BRACKETS TO REMOVABLY RECEIVE THE END PORTIONS OF LINGUAL ARCH WIRES

RELATED APPLICATIONS

This is a continuation-in-part of our copending application, Ser. No. 030,442, filed Mar. 25, 1987 now U.S. Pat. No. 4,799,883, issued Jan. 24, 1989 for ORTHODONTIC MIRROR IMAGE BRACKETS TO REMOVABLY RECEIVE THE END PORTIONS OF LINGUAL ARCH WIRES.

BACKGROUND OF THE INVENTION

The need for a lingual arch wire with supports thereof has long been recognized in dentistry. This strong wire, when supported on molars, has a variety of uses, such as to:

1. Maintain space when teeth are prematurely lost;
2. Retain arch size during and after orthodontic therapy;
3. Serve as a base for attaching auxiliary wires for tooth movement;
4. Provide anchorage, total or supplemental, for tooth movement; and
5. Regulate molar movement in all planes.

The lingual arch wires and their supports, which are used currently and have been employed by orthodontists for over three quarters of a century, should not be confused with the recent innovation of placing attachments of orthodontic brackets on the lingual surfaces of all the teeth in a dental arch to be regulated. These appliances are referred to as "Lingual Appliances".

Originally, the round lingual arch wire was fixed, by soldering it to molar bands, in turn cemented to molars. To make adjustments of the lingual arch wire or to add auxiliaries to it, the molar bands to which it was soldered had to be removed and recemented each time. This time consuming and cumbersome approach to manipulating the lingual arch wire resulted in a search for orthodontic devices which could be designed to secure the lingual arch wire in a very fixed way, and yet have it be quickly and easily removed.

Such orthodontic devices were said to make the lingual arch wire "fixed-removable". One of the first devices for a "fixed-removable" lingual arch wire was designed by John V. Mershon. The Mershon device was a bracket which consisted of a half round tube soldered vertically to a molar band. Then a half round wire dimensioned to fit the half round tube was soldered on the lingual arch wire. Thereafter, when the half round wire was fitted to the half round tube on the molar band, one end of the lingual arch wire was secured.

Later, Dr. A. Edel formed a lingual arch wire receiving bracket, which has two vertical round tubes soldered parallel to each other on the molar band. A round wire staple was adapted to fit simultaneously into the vertical tubes. This staple was then soldered to the lingual arch wire and then used in securing one end of the lingual arch wire.

Walter H. Ellis attempted to improve on Dr. Edel's bracket by using a specially formed continuous arch wire, thus eliminating a soldering operation. An oval tube was soldered vertically to the lingual of the molar band. The terminal end of the lingual arch wire was fabricated with a short, closed loop, which fitted in the vertical oval tube.

All of these prior devices, inclusive of their brackets did function, but their negative factors were: the difficulty of their fabrication, and their frequency of breakage, which was all too frequent.

Spencer R. Atkinson designed a lingual arch bracket with a horizontal sheath, which is currently available. The terminal end of the lingual arch wire was recurved on itself and then wa retained by friction in the horizontal sheath. The negative factors were and are: special pliers are needed to form the recurved end; and, a dentist may experience difficulty in placing and removing the recurved ends in the respective horizontally oriented sheath.

The Gashgarian Palatal Bar described by Fredrico V. Tent has a horizontal molar sheath similar to Atkinson's bracket. The arch wire is oriented palatally after it leaves the sheath. The arch wire is prefabricated and is presently available in four different sizes.

Wilson has made and still makes a prefabricated lingual arch wire with closed loops. These closed loops fit precisely into two vertical tubes on respective molar bands. They may be obtained from Rocky Mountain Orthodontic Supply Company in Denver, Co.

Although these prior brackets and devices were and are effective in positioning and securing lingual arch wires, a simple and more efficient approach to attaching a lingual arch wire to the molars is still needed.

SUMMARY OF THE INVENTION

The mirror image orthodontic brackets are simple and conveniently used, and considered "fixed-removable". The advantages realized in using these mirror image orthodontic bracket are:

1. No special pliers are needed to construct or manipulate the lingual arch wire;
2. The lingual arch wire is inserted and removed with respect to the occlusal direction;
3. The horizontal orientation of the bracket eliminates lingual arch wire and other installation breakage;
4. The snap-lock is positive and retains the lingual arch wire firmly in the bracket in its fixed-removable position;
5. The snap out unlocking of the lingual arch wire is simple and easy;
6. The lingual arch wire may be formed and accurately placed in the patient's mouth while the dentist remains by the dental chair;
7. Laboratory procedures are eliminated; and
8. These mirror image orthodontic brackets control molar tooth movement in all geometric planes.

When the mirror image orthodontic brackets of the invention are welded or soldered to the lingual surface of molar bands, which are in turn cemented to molars, then they are ready to fixed-removably receive a lingual arch wire having respective ends terminating in ninety degree bend portions. A mirror image orthodontic bracket has an overall elongated block configuration. One essentially vertical surface, designated as the medial surface, is provided for soldering or spot welding to a molar band. One interrupted occlusal surface is provided for presenting the entrance to a longitudinal slot which receives a horizontal end portion of a lingual arch wire. The interrupted surface may be an occlusal surface, and the lingual arch wire is moved downwardly, so the end thereof will fit into the longitudinal slot. One forward surface is provided to present an entry of this longitudinal slot. One rear surface is provided to present an exit for the longitudinal slot. One interrupted surface, opposite the occlusal surface, is provided to present the exit of a vertical hole, which joins the longitudinal slot. The vertical hole interrupts the occlusal surface proximate the distal end of the longitudinal slot. Upon securement of the lingual arch wire, the vertical hole receives the ninety degree bend portion of the arch wire.

The lingual surface, is opposite to the medial surface and has a flexure portion or portions, which resiliently, transversely, move, upon the snap-in insertion and snap out withdrawal of the horizontal end of the lingual arch wire. A protuberance is formed in the longitudinal slot to aid in securing the horizontal ends of the lingual arch wire.

The lingual arch wires, considered to be fixed-removable, are securely held in place relative to all three geometric planes to provide accurate control of the molars and the lingual arch wire itself. Each lingual arch wire is adapted accurately, without using special pliers at the dental chair locale in the presence of the patient, thereby saving time, effort and expense.

BRIEF DESCRIPTION OF THE DRAWINGS

The orthodontic mirror image brackets in several embodiments are illustrated in the drawings in respect to their several in use positions, wherein the lingual arch wire or portions thereof are also illustrated, inclusive of an orthodontic band or portions thereof. In the drawings:

FIG. 11 is a perspective view of a fourth embodiment of the invention;

FIG. 12 is a side elevational view thereof;

FIG. 13 is a cross-sectional view taken on the line 13—13 of FIG. 11 and viewed in the direction of the arrows; and, FIG. 14 is a front elevational view of the embodiment of FIG. 11.

DESCRIPTION OF THE PREFERRED EMBODIMENTS

The orthodontic mirror image brackets 20, 21, illustrated throughout the drawings, when installed in a person's mouth, via their securement to respective molar bands 22, which in turn are secured to a patient's molars 24, make it conveniently and quickly possible for a dentist, who practices orthodontics, i.e. an orthodontist, to fit a lingual arch wire 26, without using special pliers, yet with accuracy, while at a dental chair local, to a patient, thereby saving time, effort and expense.

Figure 1:
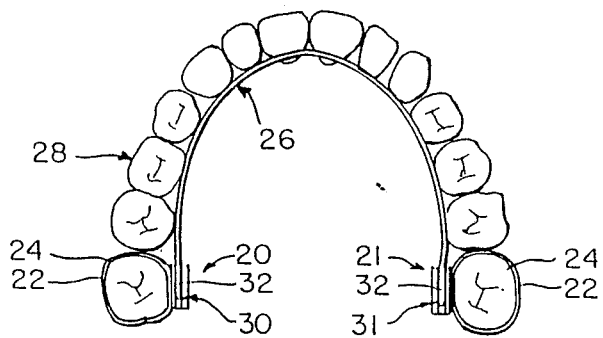
FIG. 1 is a bottom plan view of a dental arch having a lingual arch wire secured by the orthodontic mirror image brackets of the invention.

In the occlusal view of FIG. 1 of a person's full upper dental arch 28, a respective pair of orthodontic mirror image brackets 20, 21 are shown, one 20 on the left being the mirror image of the other 21 on the right. Each bracket 20, 21 is secured, such as by spot welding or soldering, to a standard molar band 22. Each band 22 in turn, is cemented to a second molar 24, as shown, or to a first molar, not shown. The brackets 20, 21 receive the respective ends 30, 31 and the end horizontal portions 32 of the lingual arch wires 26, each of which also has short perpendicular portions 34 and ninety degree bend portions 36.

Figure 2:
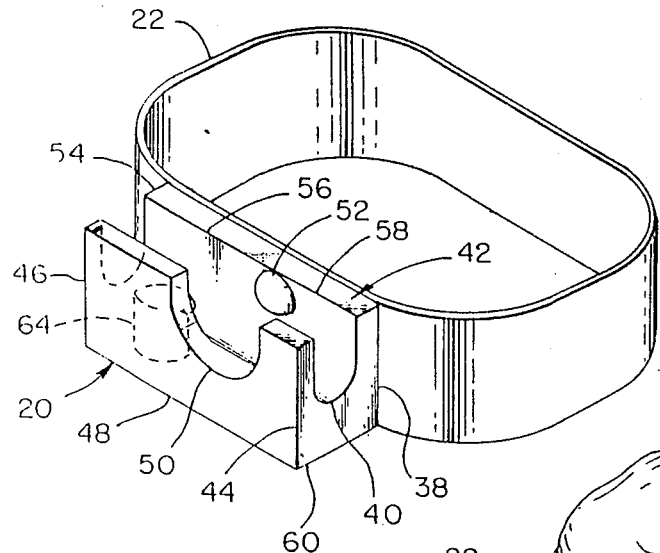
FIG. 2 is an isometric view of an orthodontic mirror image bracket secured to an orthodontic molar band.
Figure 3:
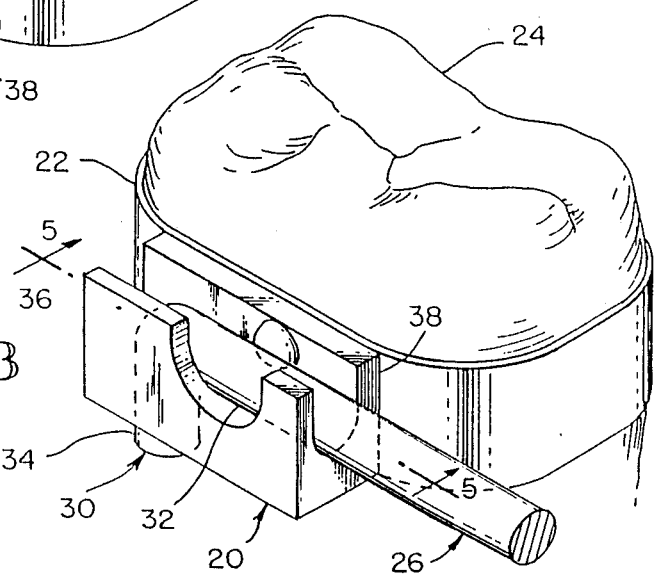
FIG. 3 is an isometric view of an orthodontic mirror image bracket and orthodontic molar band secured to a molar.

How these respective overall end portions 30, 31 of the lingual arch wire 26 are fixed-removably received and held in the brackets 20, 21, in respect to a preferred embodiment, is illustrated in FIGS. 2, 3, 4, 5 and 6. In FIG. 2, the elongated metal block bracket 20 has medial surface 38 disposed vertically and spot welded or soldered to adjacent molar band 22. Medial surface 38 is, preferably, uninterrupted. The molar band 22, in turn, is cemented to a molar 24.

Horizontal slot 40 is formed in occlusal surface 42 of the bracket 20, from the medial face 44 to the distal face 46. Slot 40 is sized to accurately accommodate lingual arch wire 26 throughout the length of its end horizontal portion 32. The medial face 44 and the distal fact 46 are both interrupted by this horizontal slot 40.

Outside wall 48 of bracket 20 is cut away for forming slot 50, which extends to the bottom of horizontal slot 40. Locking protuberance 52 is positioned on inside wall 54, on its lingual surface 56, to project into the horizontal slot 40 near its entry 58. When the end horizontal portion 32 of the lingual arch wire 26 is moved into place in the horizontal slot 40, then the slotted outside wall 48 flexes on account of slot 50 so that the horizontal portion 32 of the lingual arch wire 26 may move relative to the locking protuberance 52 into the horizontal slot 40.

Figure 4:
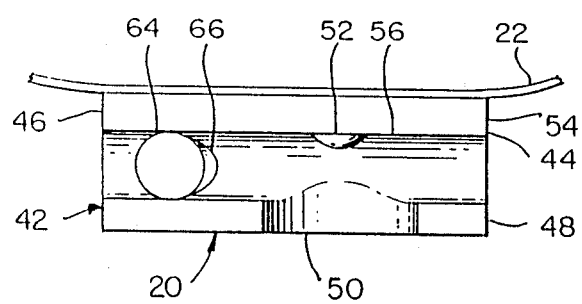
FIG. 4 is a top plan view of an orthodontic mirror image bracket of the invention.
Figure 5:
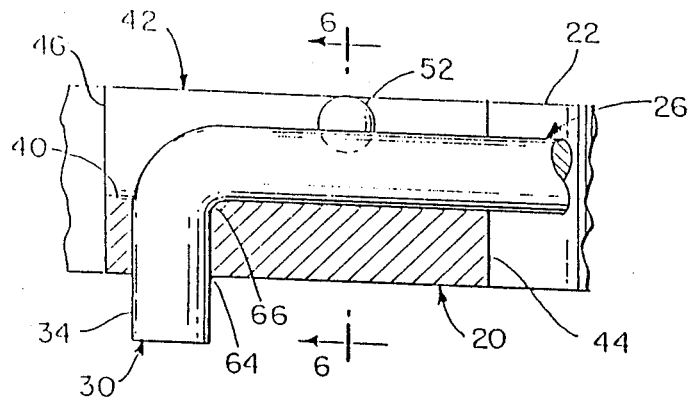
FIG. 5 is an elevational view with portions broken away of an orthodontic mirror image bracket secured to a lingual arch wire.
Figure 6:
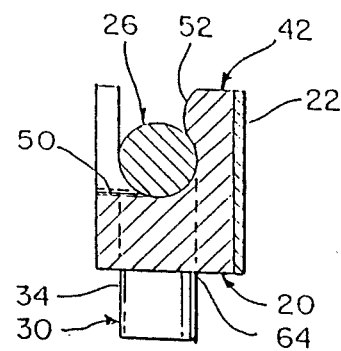
FIG. 6 is a cross-sectional view taken on line 6—6 of FIG. 5 and viewed in the direction of the arrows.

Lower horizontal surface 60 of the brackets 20, 21 is interrupted by vertical hole 64, which extends from the horizontal slot 40. The ends 30, 31 of the lingual arch wire 26, each has a ninety degree bend portion 36 and a short perpendicular portion 34 extending therefrom and insertable into vertical hole 64. Bevel portion 66, as best shown in FIG. 4, is formed between the hole 64 and the horizontal slot 40 to accommodate the ninety degree bend portion 36 of the lingual arch wire 26. Preferably the short perpendicular portion 34 extends beyond surface 60 when the lingual arch wire 26 is inserted into the bracket 20.

Mesial and distal movements of the lingual arch wire 26 are prevented by insertion of portions 34 into holes 64. Rotation of lingual arch wire 26 is also prevented because the lingual arch wire 26 is snapped into place in horizontal slot 40.

Figure 7:
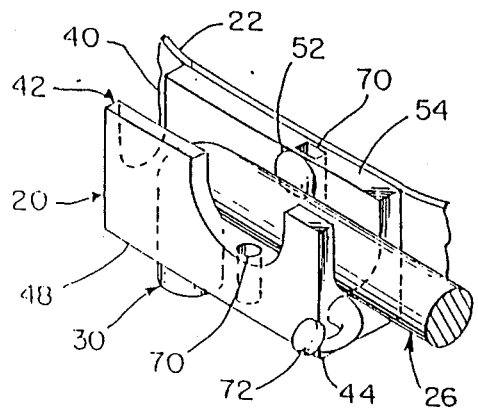
FIG. 7 is an isometric view of a second embodiment of the invention.

The orthodontic mirror image bracket 20 of FIG. 7 has a vertical hole 68 in the outsidewall 48, and a vertical hole 70 in the insidewall 54. Holes 68 and 70 may receive a passing ligature, not shown, to supplement the locking mechanism. Also, hook 72 is attached to mesial face 44, to facilitate the application of intermaxillary elastics, not shown.

Figure 8:
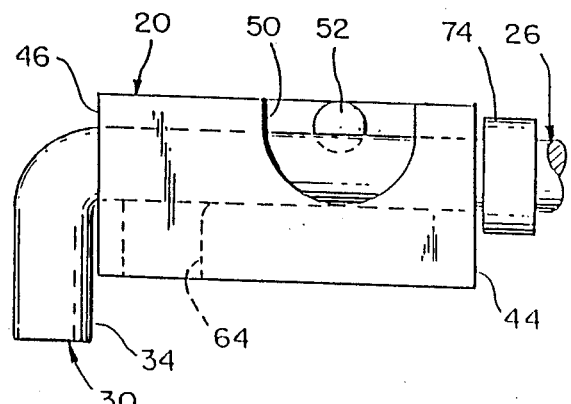
FIG. 8 is an elevational view of the embodiment of FIG. 7.

FIG. 8 discloses the short perpendicular portion 34 positioned beyond the vertical hole 64 and extending along the distal face 46 of the orthodontic mirror image bracket 20. This permits the molar 24, having its molar band 22 attached to the bracket 20, to rotate around the lingual arch wire 26 because some relatively minor rotational movement may be desirable. The short perpendicular portion 34 prevents mesial migration of the lingual arch wire 26 and stop 74 may be placed on the lingual arch wire 26 near mesial face 44 to prevent distal migration of the lingual arch wire 26.

Figure 9:
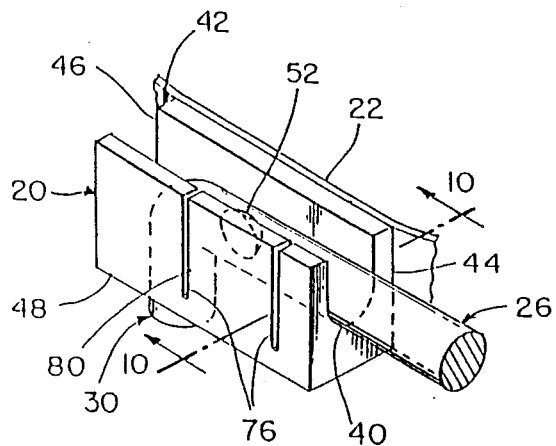
FIG. 9 is an isometric view of a third embodiment of the invention.
Figure 10:
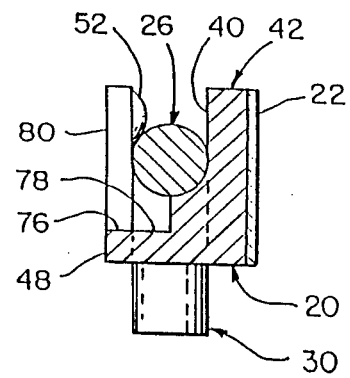
FIG. 10 is a cross-sectional view taken on the line 10—10 of FIG. 9 and viewed in the direction of the arrows.

FIGS. 9 and 10 disclose two spaced vertical cuts 76 in outer wall 48 for permitting flexure thereof. Cuts 76 extend lower than the bottom of the horizontal slot 40 and toward the middle of the bracket 20 for creating cellar well 78. The outer wall portion between these cuts 76, which flexes very well, is referred to as the spring lock segment 80.

The locking protuberance 52, in the embodiment of FIGS. 9 and 10, is positioned on spring lock segment 80. When the lingual arch wire 26 is entered into the horizontal slot 40 then it moves the spring lock segment 80 outwardly, clearing the way for entry of the lingual arch wire 26. The cellar well 78, as best shown in FIG. 10 increases the flexure capability of the spring lock segment 80. Once the end 32 is seated in slot 40, then the spring lock segment 80 may return to its initial position, thereby placing the locking protuberance 52 over the lingual arch wire 26.

The orthodontic bracket 220 of FIGS. 11-14 is similar to the brackets 20 and 21 of FIGS. 1-10. Those skilled in the art will appreciate that a conventional installation will require two of the brackets 220, but for the purposes of simplicity only one will be described herein. Naturally, the brackets will be mirror images of each other due to their opposite orientation on either side of the dental arch.

The bracket 220 of FIG. 11 is fabricated from a continuous length of metal stock, preferably a surgical grade of stainless steel. The bracket 220 has a first sidewall 222 having inner and outer wall portions 224 and 226, respectively. Second sidewall 228 has inner and outer wall portions 230 and 232, respectively. The second sidewall 228 extends accurately, upwardly and outwardly from a lower end portion of first sidewall 226 and cooperates therewith for defining an upper channel 234 and a lower channel 236. The upper and lower channels 234 and 236 are interconnected through a throat portion 238 having a width less than the width of either of the channels 234 and 236.

Second sidewall 228 has a pawl 240 with an arcuate surface 242 extending into and overlying upper channel 234. Inner wall portion 224 of second sidewall 222 has a lower arcuate surface 244 for receiving a portion of orthodontic wire 246. The surfaces 242 and 244 cooperate for causing the wire 246 to be engaged by the surface 242 of the pawl 240 and thereby pressed against the conforming surface 244 in a manner causing the wire 246 to be secured within the channel 234. The pawl 240 preferably extends the length of second sidewall 228, or at least by an amount sufficient to make certain that the wire 246 is properly secured within the bracket 220.

Second sidewall 228 has an outer corner portion 248 of substantially constant radius, as well as an inner corner portion 250 which is also of a substantially constant radius. The corner portions 248 and 250 permit the second sidewall 228 to flex relative to the first sidewall 222, in a manner permitting the wire 246 to be inserted within the channel 234. We have found that arcs of substantially constant radius should be used because they minimize stress fractures caused by bending of the second sidewall 228 during insertion and removal of the wires 246. It should be recalled that it may be necessary to insert and remove the wire 246 a number of times during the treatment program, and it is therefore necessary that cracking, breakage and the like be minimized, particularly in view of the acidic nature of the oral cavity.

We also provide a lower inner corner portion 252 at the base of channel 236, as well as an upper inner corner portion 254 where the merger with tongue 256 occurs. The corner portions 252 and 254 are, preferably, of uniform radius. The arcuate nature of the corner portions 252 and 254 minimizes any stress which could be imparted to the bracket 220 on account of the flexing of the second sidewall 228, or on account of flexing of the tongue 250 during the snap-in insertion of the wire 246.

As with the brackets 20 and 21, we provide an opening 258 in the bracket 220 for receiving the vertical portion 260 of the wire 246. The opening 258, however, extends through second wall 228 and through tongue 256, and thereby interconnects the channels 234 and 236. We prefer that the opening 258 be proximate the distal end 262, rather than the proximal end 264. Location of the vertical opening 258 proximate the distal end 262 assures that the wire 246 is supported and secured for a substantial portion of the length thereof which is subject to bending moments. This minimizes pivoting of the wire 246, and also minimizes breakage of the wire 246 as could occur on account of the application of repeated bending moments.

The first sidewall 222 terminates in a first planar surface 266 which is disposed vertically above the corresponding surface 268 of second sidewall 228. Inner wall portion 224 of first sidewall 222 terminates in an upper arcuate portion 270 which is oppositely directed relative to lower arcuate surface 244. This has the effect of increasing access to upper channel 234, thereby facilitating insertion of the wire 246.

While this invention has been described as having a preferred design, it is understood that it is capable of further modifications, uses and/or adaptations of the invention following in general the principles of the invention and including any departures therefrom falling within the scope of the invention and the limits of the appended claims.

What we claim is:

1. An orthodontic bracket, comprising:
   (a) a body having first and second ends, a first vertical sidewall for attachment to a molar band, and a second sidewall extending arcuately and upwardly away from a lower portion of said first sidewall;
   (b) a contoured slot extending between said ends and downwardly from an upper portion of said first sidewall for defining an upper channel and a lower channel permitting said second sidewall to flex outwardly relative to said first channel;
   (c) said upper channel includes a lower arcuate surface on said first sidewall upon which an orthodontic wire seats; and,
   (d) said second sidewall includes a pawl overlying said upper channel and extending substantially the length thereof for engaging and maintaining an orthodontic wire in said upper channel and against said lower arcuate surface.

2. The bracket of claim 1, wherein:

(a) said pawl has an arcuate surface directed toward said upper channel; and,
(b) said lower and pawl arcuate surfaces are defined by a common radius.

3. The bracket of claim 1, wherein:
(a) said first sidewall terminates in a first surface; and,
(b) said second sidewall terminates in a second surface and said second surface is disposed below said first surface.

4. The bracket of claim 3, wherein:
(a) said first and second surfaces are parallel.

5. The bracket of claim 1, wherein:
(a) said first sidewall has an inner wall portion merging with said upper channel, and said inner wall portion is arcuate and directed away from said upper channel for providing an enlarged opening for said upper channel.

6. The bracket of claim 1, wherein:
(a) a vertical opening is disposed in said second sidewall and extends from said lower channel.

7. The bracket of claim 6, wherein:
(a) said opening is disposed proximate said first end.

8. The bracket of claim 6, wherein:
(a) said vertical opening extends through said upper channel.

9. The bracket of claim 1, wherein:
(a) said sidewall has an outer wall and an inner wall portion and said outer wall portion is uninterrupted.

10. The bracket of claim 9, wherein:
(a) said inner and outer wall portions each includes a lower corner portion, and said corner portions are each defined by a constant radius.

11. The bracket of claim 10, wherein:
(a) said lower channel includes inner upper and lower corner portions, and said inner upper and lower corner portions are arcuate and defined by radii of common dimension.

12. An orthodontic bracket, comprising:
(a) a metal body having first and second spaced ends, a first vertical sidewall, and a second sidewall extending arcuately and upwardly away from a lower portion of said first sidewall;

(b) said first and second sidewalls have inner and outer wall portions, and said inner wall portions are interconnected and define upper and lower interconnected channels;
(c) said second sidewall inner wall portion has an arcuate pawl extending into and overlying said upper channel;
(d) said first sidewall inner wall portion has a lower arcuate surface for receiving an orthodontic wire, said lower surface cooperates with said pawl for causing the wire to be engaged by said pawl and thereby forced against said lower surface for being secured within said upper channel; and,
(e) said second sidewall inner and outer wall portions have cooperating lower corner portions for permitting said second sidewall to flex outwardly relative to said first sidewall so that the orthodontic wire may be inserted into said upper channel.

13. The bracket of claim 12, wherein:
(a) a vertical opening is disposed in said body in communication with said channels and extending through said second sidewall.

14. The bracket of claim 12, wherein:
(a) said pawl extends the length of said second sidewall; and,
(b) said pawl and said lower surface are defined by a common radius.

15. The bracket of claim 14, wherein:
(a) said first sidewall terminates in a first upper surface; and,
(b) said second sidewall terminates in a second upper surface, and said second upper surface is disposed below said first upper surface.

16. The bracket of claim 12, wherein:
(a) said channels are interconnected through a throat portion, and said throat portion has a width less than the width of said upper and lower channels.

17. The bracket of claim 15, wherein:
(a) said first sidewall inner portion bas an arcuate portion merging into said first upper surface and said arcuate portion is oriented oppositely to said lower surface for providing enlarged access to said upper channel.

* * * * *